United States Patent [19]

Harandi et al.

[11] Patent Number: 4,990,712
[45] Date of Patent: Feb. 5, 1991

[54] INTEGRATED CRACKING, ETHERIFICATION AND OLEFIN UPGRADING PROCESS

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 524,948

[22] Filed: May 18, 1990

[51] Int. Cl.$^5$ .................... C07C 41/06; C07C 2/00
[52] U.S. Cl. ...................... 585/324; 585/310; 585/314; 585/322; 585/315; 585/328; 585/329; 585/830; 585/860; 44/309; 44/446; 44/448; 568/697; 568/699
[58] Field of Search ............... 585/324, 310, 314, 322, 585/315, 328, 329, 830, 860; 44/77, 56; 568/697, 699

[56] References Cited

U.S. PATENT DOCUMENTS

| | | | |
|---|---|---|---|
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,411,773 | 10/1983 | Gross | 208/164 |
| 4,774,365 | 9/1988 | Chen et al. | 585/324 |
| 4,788,365 | 11/1988 | Harandi et al. | 585/312 |
| 4,826,507 | 5/1989 | Harandi et al. | 44/77 |
| 4,827,046 | 5/1989 | Harandi et al. | 585/310 |
| 4,830,635 | 5/1989 | Harandi et al. | 44/56 |
| 4,929,780 | 5/1990 | Wright et al. | 585/324 |

Primary Examiner—Chung K. Pak
Attorney, Agent, or Firm—Alexander J. McKillop; Charles J. Speciale; Robert B. Furr, Jr.

[57] ABSTRACT

Gasoline octane number and yield are improved while excess fuel gas production is decreased in a catalytic cracking process by integrating etherification and oxygenate/aliphatic upgrading processes into the catalytic cracking unit product fractionation section.

12 Claims, 3 Drawing Sheets

INTEGRATED CRACKING, ETHERIFICATION AND OLEFIN UPGRADING PROCESS

FIELD OF THE INVENTION

The present invention relates to a process for producing high octane gasoline from light olefinic streams produced in a hydrocarbon cracking process. More specifically, the invention relates to an integrated three-stage process which includes a first cracking stage, a second intermediate product deacidification and fractionation stage, and a third intermediate product upgrading stage.

BACKGROUND OF THE INVENTION

Environmental regulations restricting the use of octane enhancing lead additives for internal combustion engines as well as the shift in the automotive industry toward more efficient higher compression ratio engines have prompted the petroleum refining industry to seek alternate processes for meeting the demand for high octane unleaded gasoline.

In order to meet these requirements, the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the impact on the cost of gasoline is significant.

Catalytic cracking processes manufacture a major segment of the total gasoline pool produced in modern oil refineries by upgrading gas oil and heavier feedstreams to a lighter product slate including gasoline and distillate as well as $C_4-$ aliphatics rich in olefins. Examples of such catalytic cracking processes are described in P. B. Venuto and E. T. Habib, Jr., *Fluid Catalytic cracking with Zeolite Catalysts* (1979) as well as U.S. Pat. Nos. 2,383,686 to Wurth; 2,689,210 to Leffer; 4,093,537 to Gross et al.; 4,118,338 to Gross et al.; and 4,411,773 to Gross, Which patents are incorporated by reference herein.

To increase the overall yield of high octane gasoline from catalytic cracking units, processes have been developed which upgrade the $C_4-$ by-products of the cracking process. With the advent of these light aliphatics upgrading processes, the demands on the catalytic cracking unit product fractionation section have also changed. Specifically, the $C_4$ aliphatics upgrading processes operate at relatively high temperature conditions, typically above about 700° F. For this reason, the $H_2$, $H_2S$, and mercaptan sulfur contents of the $C_4-$ aliphatic streams from the catalytic cracking unit product fractionation section are critical, not only to meet product specifications and to prevent accelerated catalyst deactivation, but also to assure safe and reliable unit operation using the most economical materials of construction. It has been found that levels of $H_2S$, $H_2$, and mercaptan sulfur levels which were completely acceptable for lower temperature light aliphatics upgrading processes such as HF or $H_2SO_4$ catalyzed alkylation can markedly accelerate corrosion, pitting and cracking in carbon steel and lower alloy vessels under the more severe temperature conditions associated with the catalytic upgrading processes presently under consideration. Thus it would be desirable to provide the light aliphatics upgrading process associated with the catalytic cracking unit with a $C_2-C_4$ aliphatic stream which is relatively free from $H_2S$, $H_2$, and mercaptan sulfur.

Catalytic cracking process units typically include a main fractionator, commonly called the column, which receives cooled reactor effluent from the catalytic cracking process. The main column fractionates this reactor effluent into a plurality of streams including clarified slurry oil, heavy cycle oil, light cycle oil, unstabilized gasoline and an overhead gas stream rich in $C_4-$ olefins. The gasoline and lighter components are then further fractionated in an unsaturate gas plant which typically includes, in order, a deethanizer absorber, a debutanizer and a depropanizer.

The deethanizer absorber splits the gasoline and lighter material into a $C_2-$ overhead gas stream and a $C_3+$ bottoms stream. The $C_2-$ overhead gas stream may optionally be treated in a sponge absorber to further sorb $C_3+$ components before acidic components such as hydrogen sulfide, carbon dioxide and hydrogen cyanide are removed in a purification sorption column. Having been treated to reduce its acidic gas content, the deethanizer absorber overhead stream is then charged to a fuel gas header to be burned for fuel in the refinery complex.

The deethanizer absorber bottom stream is then charged to a debutanizer fractionator where it is split into a $C_5+$ gasoline stream rich in olefinic components and a $C_3-C_4$ overhead stream. The debutanizer fractionator is typically designed to meet a bottom stream gasoline volatility specification requiring vapor pressure of less than about 10 psi. Finally, the debutanizer overhead stream, rich in $C_3-C_4$ olefins, may be fractionated into a propane/propylene overhead stream and a butane/butylene bottoms stream. This step is most often employed when additional light aliphatics upgrading capacity is available, for example, an alkylation process unit for converting iso- and normal $C_4$ aliphatics to high octane alkylate gasoline. The $C_3-$ depropanizer or debutanizer overhead stream may be sold as LPG, but first must be treated in a mercaptan sulfur removal process to meet sulfur content specifications. One example of such a process is the Merox process (trademark and/or service mark of UOP, Inc.).

The incremental volume of $C_2-$ fuel gas generated by a catalytic cracking process may increase the total refinery fuel gas volume beyond that needed to fulfill its fuel gas consumption and sales requirements. To assure compliance with environmental regulations governing content and volume of gases exhausted to the atmosphere, fuel gas production is limited to the total volume which can be consumed within the refinery, sold to consumers beyond the battery limits of the refinery, or flared in accordance with the applicable environmental permits. Thus if the incremental volume of fuel gas generated by the catalytic cracking unit exceeds the capacity of facilities for its disposition, the cracking unit feedrate or reaction severity must be reduced. Neither option is economically desirable. The ideal solution would be to decrease fuel gas volume by shifting the overall yield from the catalytic cracking unit away from $C_2-$ components and toward more valuable high octane $C_5+$ gasoline. The acid gas components of the catalytic cracking unit reactor effluent stream tend, however, to be carried with ethane and ethylene. Clearly, then, the problem of excess fuel gas production cannot be solved merely by shifting the cut points in a conventional catalytic cracking product fractionation section because the downstream light aliphatics upgrading process would be exposed to hydrogen and acid gases under severe temperature conditions.

A number of acid gas removal processes are commercially available for treating this overhead stream including chemical solvent as well as physical sorption processes. Chemical solvent techniques include countercurrent contacting with monoethanolamine (MEA), diethanolamine (DEA) and hot potassium carbonate. Physical sorption techniques employ solid sorbents such as molecular sieves, activated charcoal and iron sponge.

Conventionally, these acid gas removal processes are installed downstream of the sponge absorber and debutanizer. Consequently, the acid gases are carried through the various upstream separation processes of the USGP including the absorber-deethanizer, sponge absorber and debutanizer. This configuration tends to increase the rate of acid gas induced corrosion of a large portion of the vessels and ancillary equipment in the USGP, leading to increased maintenance operations and plant downtime. Under the more severe temperature conditions of catalytic aliphatics upgrading processes, streams containing these acidic components readily attack carbon steel and the lower chromium- and molybdenum-containing steel alloys, and may cause cracking, pitting, blistering, or general thinning.

The available light aliphatics upgrading processes, include catalytic aromatization, oligomerization and etherification. Catalytic aromatization converts the light aliphatics over a catalyst, for example a medium-pore zeolite catalyst such as ZSM-5, to a product mixture rich in aromatics. Oligomerization and olefin interconversion may employ similar catalysts, but are typically conducted under less severe temperature conditions. Etherification reacts olefins with alcohols to form ethers useful as octane-enhancing gasoline additives. For example, isobutylene may be reacted with methanol over an acidic catalyst to produce methyl-tertiary butyl ether (MTBE) and that isoamylenes may be reacted with methanol over an acidic catalyst to produce tertiary-amyl methyl ether (TAME).

In U.S. Pat. Nos. 4,830,635; 4,826,507; and 4,788,365 to Harandi and Owen the ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction.

The process for the conversion of methanol to olefins is but one in a series of analogous processes based upon the catalytic capabilities of zeolites. Depending on various conditions of space velocity, temperature and pressure methanol, and lower oxygenates in general, can be converted in the presence of zeolite type catalyst to olefins which may then oligomerize to provide gasoline or distillate or be converted further to produce aromatics. In another application of zeolite catalysis, light olefins can be interconverted or redistributed at low pressure and high temperature to produce higher olefins rich in isoalkenes.

Recent developments in zeolite catalyst and hydrocarbon conversion processes have created interest in using olefinic feedstocks for producing $C_5+$ gasoline, diesel fuel, and higher boiling hydrocarbon products. In addition to the basic work derived from medium pore zeolites such as ZSM-5, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_3$-$C_5$ alkenes. In U.S. Pat. Nos. 3,960,978 and 4,021,502, Plank, Rosinski and Givens disclose conversion of $C_2$-$C_5$ olefins, alone or in admixture with paraffinic components into higher hydrocarbons over crystalline zeolites having controlled acidity. Garwood et al. have also contributed improved processing techniques to the MOGD system as in U.S. Pat. Nos. 4,150,062; 4,211,640; and 4,227,992. The conversion of olefins to gasoline using a fluidized catalyst bed is the subject of U.S. patent application Ser. No. 006407 to Owen et al. The above identified disclosures are incorporated herein by reference. The MOGD process may produce low octane gasoline. This disadvantage requires further downstream processing of the product so produced in order to provide a gasoline product with useful road octane value. Improvement of the process to provide an instant higher octane value gasoline product has been a much sought after objective in that field of art.

These two processes, etherification and olefin oligomerization/interconversion have been advantageously integrated to provide a high octane ether-rich gasoline product from aliphatic hydrocarbon and lower alkyl alcohol feedstreams. The Mobil Olefins to Ethers and Gasoline (MOEG) process produces methyl tert-butyl ether (MTBE) and/or tertiary amyl methyl ether (TAME) by a two-step reaction sequence utilizing a catalytic etherification step as described above, followed by a zeolite catalysis to convert unreacted alcohol and olefins in the etherification effluent MTBE and TAME are formed conventionally by contacting a stream rich in isobutylene and isoamylene in the presence of a acid catalyst, e.g. a sulfonic acid resin catalyst such as Amberlyst 15, which catalyzes the iso-olefin/alcohol reaction. This process is detailed in U.S Pat. Nos. 4,830,635; 4,826,507; and 4,788,365 to Harandi and Owen, which are incorporated herein by reference for details of the MOEG process.

Thus it is clear that a process for shifting product yield in a catalytic cracking unit away from $C_4-$ light aliphatics, particularly $C_2-$ fuel gas, to favor production of high octane gasoline would provide substantial operational and economic benefits. Further, it would be desirable to provide the light olefin upgrading section of such a process with a feedstock of sufficient purity to meet the application environmental standards and product quality specifications while also avoiding the incremental capital costs associated with alloyed process equipment.

SUMMARY OF THE INVENTION

The present inventive process a first cracking stage, a second intermediate product deacidification/ fractionation stage, and a third intermediate product upgrading stage to reduce the total $C_4-$ gas production from the cracking process while increasing $C_5+$ gasoline volume and octane number. By shifting yield away from $C_4-$ gas toward $C_5+$ liquid, fuel gas as well as LPG production are beneficially decreased, thus minimizing the effects of refinery fuel gas volume limitations on the cracking process while also decreasing LPG mercaptan sulfur removal treatment costs. Further, the present process limits the concentrations of $H_2S$, $H_2$, $N_2$, and mercaptan sulfur flowing to the light aliphatics upgrading reaction zone minimize the use of nickel- and chromium-alloyed process equipment. Still further, the present integrated process limits the flow of these undesirable acid gas constituents to the light aliphatics upgrading reaction zone without sacrificing process flexibility.

The terms "cracking stage" and "cracking process" as used herein encompass thermal cracking processes, e.g. delayed coking, catalytic cracking processes, e.g. Thermofor Catalytic Cracking (TCC) and Fluid Catalytic Cracking (FCC), as well as steam cracking commonly used in industry for ethylene production. In the most preferred embodiment of the invention, the cracking stage comprises a Fluid Catalytic Cracking (FCC) process.

In a first method aspect, the invention provides an integrated process for upgrading gasoline and lighter products from a cracking process comprising the steps of:

compressing and cooling a $C_4-$ cracking process product stream to provide an ethene-rich vapor stream and a first condensed $C_3+$ aliphatic stream;

countercurrently contacting the ethene-rich vapor stream and the condensed $C_3+$ aliphatic stream with a $C_5+$ liquid sorbent stream comprising cracked gasoline under superatmospheric pressure in an absorber column to sorb a major portion of $C_2+$ components;

recovering a methane-rich overhead stream from the absorber column;

recovering an absorber bottom stream from the absorber column containing $C_2+$ components;

fractionating the absorber bottom stream in a first fractionator to evolve an overhead stream rich in $C_2-C_5$ aliphatics and a $C_5+$ cracked gasoline stream;

contacting at least a portion of the first fractionator overhead stream with an acid etherification catalyst in a guard bed zone to sorb at least a portion of the catalyst poisons in the debutanizer overhead stream including nitrogen-containing compounds;

mixing effluent from the guard bed with an amount of a primary alcohol sufficient to etherify the $C_4-C_5$ components of the guard bed effluent stream;

contacting the mixture of primary alcohol and guard bed effluent with an acid etherification catalyst under etherification conversion conditions to form a product mixture containing high-octane gasoline rich in ethers as well as unconverted oxygenate and $C_4-$ aliphatic hydrocarbons; fractionating the high octane gasoline product mixture in a second fractionator into an overhead stream containing unconverted oxygenate and $C_4-$ aliphatics and a bottom stream containing ether-rich high octane gasoline; and contacting the second fractionator overhead stream with a zeolite having a Constraint Index between about 1 and about 12 under conversion conditions to upgrade the unconverted oxygenate and aliphatics contained in the second fractionator overhead stream to $C_5+$ gasoline.

In a second method aspect, the invention provides a process for upgrading light olefinic crackate gas from hydrocarbon cracking comprising the sequential steps of:

compressing and cooling a $C_4-$ cracking process product stream to provide an ethene-rich vapor stream and a first condensed $C_3+$ aliphatic stream;

deacidifying said ethene-rich vapor stream and said first condensed $C_3+$ aliphatic stream by countercurrently contacting said ethene-rich vapor stream and said first condensed $C_3+$ aliphatic stream with acid absorbant; countercurrently contacting said deacidified ethene-rich vapor stream and said deacidified condensed $C_3+$ aliphatic stream with a $C_5+$ liquid sorbent stream comprising a cracked gasoline under superatmospheric pressure in an absorber column to sorb a major portion of $C_2+$ components;

recovering a methane-rich overhead stream from said absorber column;

recovering an absorber bottom stream from said absorber column containing $C_2+$ components; fractionating said absorber bottom stream to evolve an overhead stream rich in $C_2-C_5$ aliphatics and a $C_5+$ cracked gasoline bottom stream; and contacting said $C_2-C_5$ overhead stream with a zeolite having a Constraint Index between about 1 and about 12 under conversion conditions to upgrade aliphatics contained in said $C_2-C_5$ overhead stream to a product stream enriched in $C_5+$ liquid hydrocarbons.

In its apparatus aspects, the invention includes an apparatus for upgrading light olefinic crackate gas from hydrocarbon cracking comprising:

a compressor for increasing the pressure of a $C_4-$ cracking process product stream;

a cooler for at least partially condensing said compressed $C_4-$ stream of (a), above;

an accumulator drum for receiving an at least partially condensed $C_4-$ stream, said accumulator drum having a first outlet conduit positioned in an upper section of said accumulator drum for withdrawing ethene-rich vapor and a second outlet conduit positioned in a lower section of said accumulator drum for withdrawing liquid containing $C_3+$ components;

an absorber tower for countercurrently contacting said ethene-rich vapor and said liquid containing $C_3+$ components with a $C_5+$ liquid sorbent, said absorber tower being in communication with said accumulator drum via said first and said second outlet conduits, said absorber tower having sufficient condenser, reboiler and fractionation capacity to provide an overhead stream rich in methane, said absorber tower optionally containing a stripping zone;

a first fractionator for fractionating a bottom stream withdrawn from said absorber tower into a $C_5+$ cracked gasoline bottom stream and an overhead stream rich in $C_2-C_5$ aliphatics;

a valved alcohol injection conduit for admixing a controlled quantity of alcohol with said first fractionator overhead stream;

an etherification reactor for contacting said admixture of said alcohol and said first debutanizer fractionator overhead stream with an acid etherification catalyst under etherification conversion conditions to form a product mixture containing high octane gasoline rich in ethers; a second fractionator for separating said etherification reactor product mixture into an overhead stream containing unconverted alcohol and $C_4-$ aliphatics and a bottom stream of ether-rich high octane gasoline; and an alcohol/aliphatics upgrading reactor for contacting said second debtanizer overhead stream with a composite catalyst containing a zeolite having a Constraint Index of between about 1 and 12 under conversion conditions whereby a product stream containing $C_5+$ gasoline is formed.

DETAILED DESCRIPTION

Figure 1:
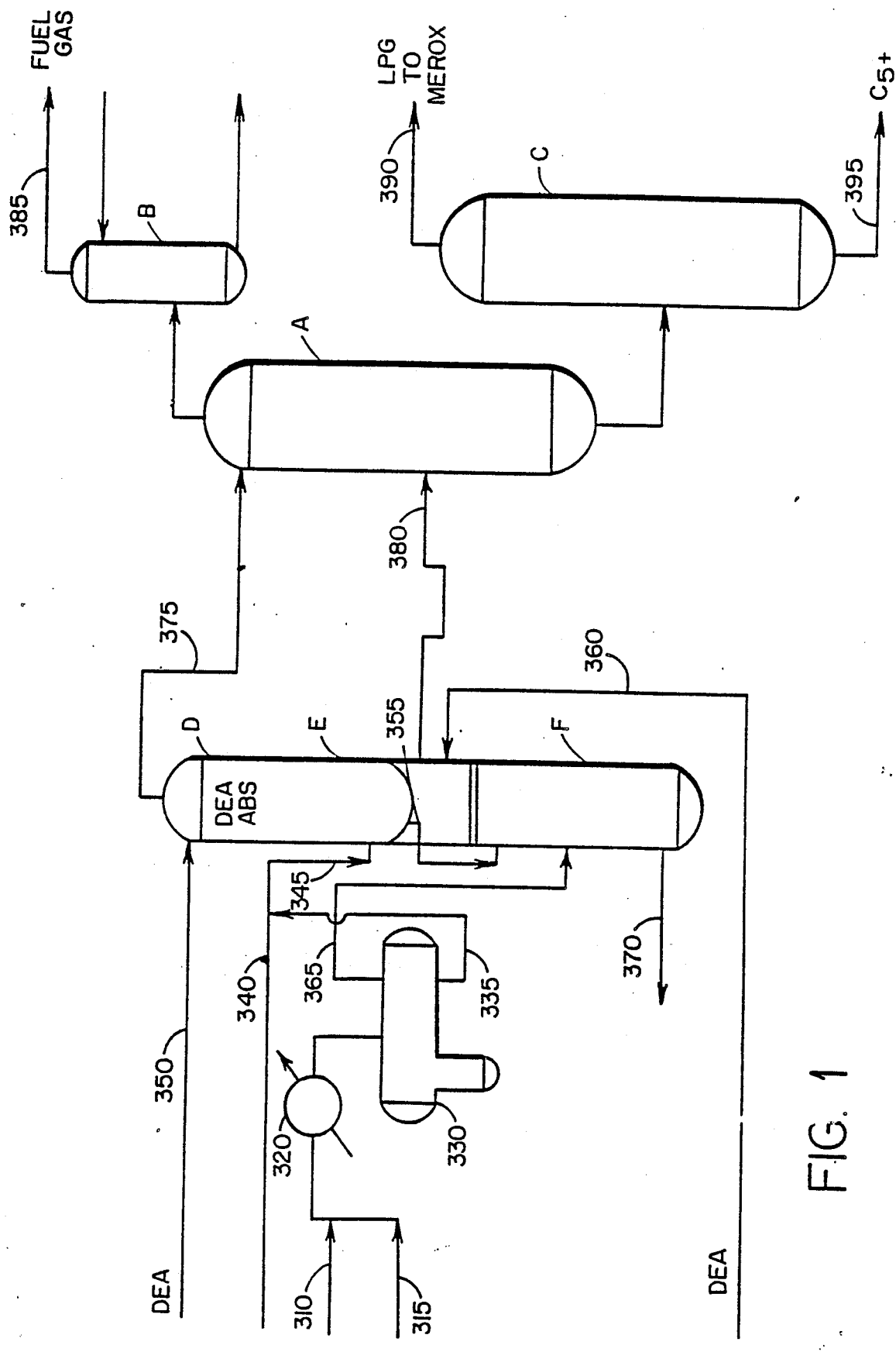
FIG. 1 is a simplified schematic diagram showing the major processing steps of a first embodiment of the intermediate product fractionation section of the process of the present invention.

In a preferred embodiment, the present process comprises three processing stages: a first catalytic cracking stage, a second intermediate product fractionation stage, and a third light aliphatics upgrading reaction stage. The first catalytic cracking stage comprises any suitable catalytic cracking configuration, as described more fully hereinbelow. The second stage fractionates and purifies the $C_9-$ intermediate product streams from the catalytic cracking process to prolong catalyst life in the downstream aliphatics upgrading stage, to achieve the desired purity both in the fuel gas and in the finished products.

The aliphatics upgrading stage may comprise aromatization, oligomerization, etherification or a combination of oligomerization and etherification. In the preferred embodiment of this invention, the aliphatics are upgraded first via etherification, which comprises reacting an alcohol, preferably a primary alcohol such as methanol with a hydrocarbon feedstock containing olefins and particularly isoolefins such as isobutene to produce methyl tertiary butyl ethers and other ethers, and then unconverted olefins and alcohol are upgraded via oligomerization.

The Catalytic Cracking Stage

In the first stage of the present process, a heavy hydrocarbon feedstock, for example, a gas oil is cracked to a lighter product slate including distillates, gasoline, and $C_4-$ aliphatics. The fluid catalytic cracking (FCC) process is most preferred for this first stage and has become well-established in the petroleum refining industry for converting higher boiling petroleum fractions into lower boiling products, especially gasoline.

In the fluid catalytic process, a finely divided solid cracking catalyst is used to promote the cracking reactions which take place in the feed. The catalyst is used in a very finely divided form, typically with a particle size range of 20-300 microns, with an average of about 60-75 microns, in which it can be handled like a fluid (hence the designation FCC) and in this form it is circulated in a closed cycle between a cracking zone and a separate regeneration zone. In the cracking zone, hot catalyst is brought into contact with the feed so as to effect the desired cracking reactions after which the catalyst is separated from the cracking products which are removed from the cracking reactor to the associated fractionation equipment for separation and further processing. During the cracking reaction, coke is deposited on the catalyst. This deposit of coke masks the active sites and temporarily deactivates the catalyst. Such temporarily deactivated catalyst is commonly called spent catalyst. The catalyst must then be regenerated before it can be reused. Fortunately, the coke deposit can be made to serve a useful purpose. Cracking is an endothermic reaction. Although, in principle, heat could be supplied by raising the temperature of the hydrocarbon feed prior to contact with the catalyst, this would thermally crack the feed so that very little control could be effected over the product distribution. Additionally, the coke formed would deposit on furnace tubes and other equipment used for heating and conveying the feed to the cracker, causing operational problems. For this reason, it is generally preferred to supply the heat to the cracking reaction by means of the catalyst. The feed may, however, be preheated to a certain degree in order to maintain an appropriate heat balance in the cycle.

Heat for the catalytic cracking process is supplied by the regeneration step in which the spent catalyst is subjected to oxidative regeneration to remove the coke. This coke-burning step is strongly exothermic and raises the regenerated catalyst temperature such the the sensible heat imparted to the catalyst during regeneration is sufficient to supply the endothermic heat of reaction for the cracking step.

The regeneration takes place in a separate regenerator vessel. Catalyst is maintained in a fluidized bed in a lower section of the regenerator vessel and an oxygen-containing gas, usually air, flows through a distribution grid which is designed to provide efficient mixing of air with the spent, coked catalyst. During the regeneration step, the coke on the spent catalyst is oxidized and the heat from the oxidation is transferred to the catalyst to raise its temperature to the requisite level for continuing the cracking reactions. The hot freshly-regenerated catalyst is then returned to the cracking zone for contact with further feed together with any recycle. Thus, the catalyst circulates continuously in a closed cycle between the cracking zone and the regenerating zone with heat for the endothermic cracking reactions being supplied in the regenerator by oxidative removal of the coke deposits which are laid down during the cracking portion of the cycle. In order to maintain the desired level of catalyst activity and selectivity, a portion of the circulating inventory of catalyst may be withdrawn intermittently or continuously with fresh, make-up catalyst being added to compensate for the withdrawn catalyst and the catalyst losses which occur through attrition and loss of catalyst from the system.

A further description of the catalytic cracking process and the role of regeneration may be found in the monograph, "Fluid Catalytic Cracking With Zeolite Catalysts", Venuto and Habib, Marcel Dekker, New York, 1978. For additional details of FCC operation, see U.S. Pat. Nos. 2,383,636 to Wirth; 2,689,210 to Leffer; 3,338,821 to Moyer et al.; 3,812,029 to Snyder, Jr.; 4,093,537 to Gross et al.; and 4,218,306 to Gross et al., the disclosures of which are incorporated by reference as if set forth at length herein.

A particularly preferred FCC configuration is disclosed in U.S. Pat. No. 4,840,928 to Harandi and Owen which teaches a fluid catalytic cracking (FCC) process in which catalyst withdrawn from the regenerator is cooled by direct contact with an alkane-rich stream in an external catalyst cooler, and is incorporated by reference as if set forth at length herein for a detailed description of a fluid catalytic cracking process. Details of FCC operation, and particularly the details of separating the fluidized catalyst from the reaction products are also taught in U.S. Pat. Nos. 4,043,899 to Anderson; 4,404,095 to Haddad; 4,502,947 to Haddad; 4,579,716 to Krambeck; 4,581,205 to Schatz; 4,588,558 to Kam; 4,606,814 to Haddad; 4,623,446 to Haddad; 4,624,772 to Krambeck; 4,654,060 to Haddad; U.S. Patent incorporated by reference as if set forth at length herein.

Intermediate Product Fractionation

The sequence of deacidification and separation steps in the second stage of the present process, intermediate product fractionation, is critical to achieving the beneficial results of the invention. Referring to FIG. 1, the major processing steps of the intermediate product fractionation stage of the present process are described. In this configuration, the principal separation operations of the USGP represented by deethanizer-absorber zone A, sponge absorber zone B and debutanizer zone C are located downstream of amine absorber operations. This is achieved by installing alkanolamine absorber D containing two amine absorption zones E and F upstream of the aforestated separation zones. Examples of suitable alkanolamines include monoethanolamine, diethanolamine, triethanolamine, and methyl diethanolame, merely to name a few. Amine absorption zones E and F are interconnected such that amine can flow from zone E to zone F. In a preferred configuration, compressor outlet gases from line 310 and interstage liquids from line 315 are cooled in exchanger 320 and separated in vapor/liquid accumulator 330. The liquid fraction is withdrawn from a lower section of vapor/liquid accumulator 330 via line 335 and is mixed with an unstabilized gasoline feedstream from line 340. The mixture of liquid from accumulator 330 and the unstabilized gasoline is introduced into a bottom portion of amine absorber zone E in countercurrent flow with a lean diethanolamine (DEA) mixture introduced into a top portion of zone E. Partially spent DEA is passed via line 355 to an upper portion of zone F in combination with fresh DEA which is added through line 360. The gaseous fraction is passed through line 365 to a lower portion of zone F in countercurrent contact with DEA. Rich DEA is withdrawn from a lower portion of zone F. The deacidified unstabilized gasoline stream is passed overhead through line 375 from zone E to an upper portion of absorber deethanizer A. The deacidified vapor fraction is transferred via line 380 from zone F to a middle portion of deethanizer A. From the deethanizer-absorber a deacidified overhead is treated in sponge absorber B to produce deacidified fuel gas which is charged to the refinery fuel gas system (not shown) through line 385. The bottom fraction from zone A is separated in debutanizer C to produce deacidified LPG which is taken overhead through line 390 and deacidified $C_5$ hydrocarbons which are withdrawn as the bottom fraction through line 395.

In the intermediate product fraction stage as described in FIG. 1, FCC unstabilized gasoline and the high pressure separator liquids are mixed and amine treated upstream of the deethanizer-absorber. Preferably, about 50-80% of the total amine circulation rate is sent to this amine absorber The deethanizer-absorber vapor feed is then sent to another amine absorber where preferably 20-50% of the total amine circulation rate is fed to the absorber upper tray and the rich amine from the other amine absorber is fed to a few trays below the upper tray.

Figure 2:
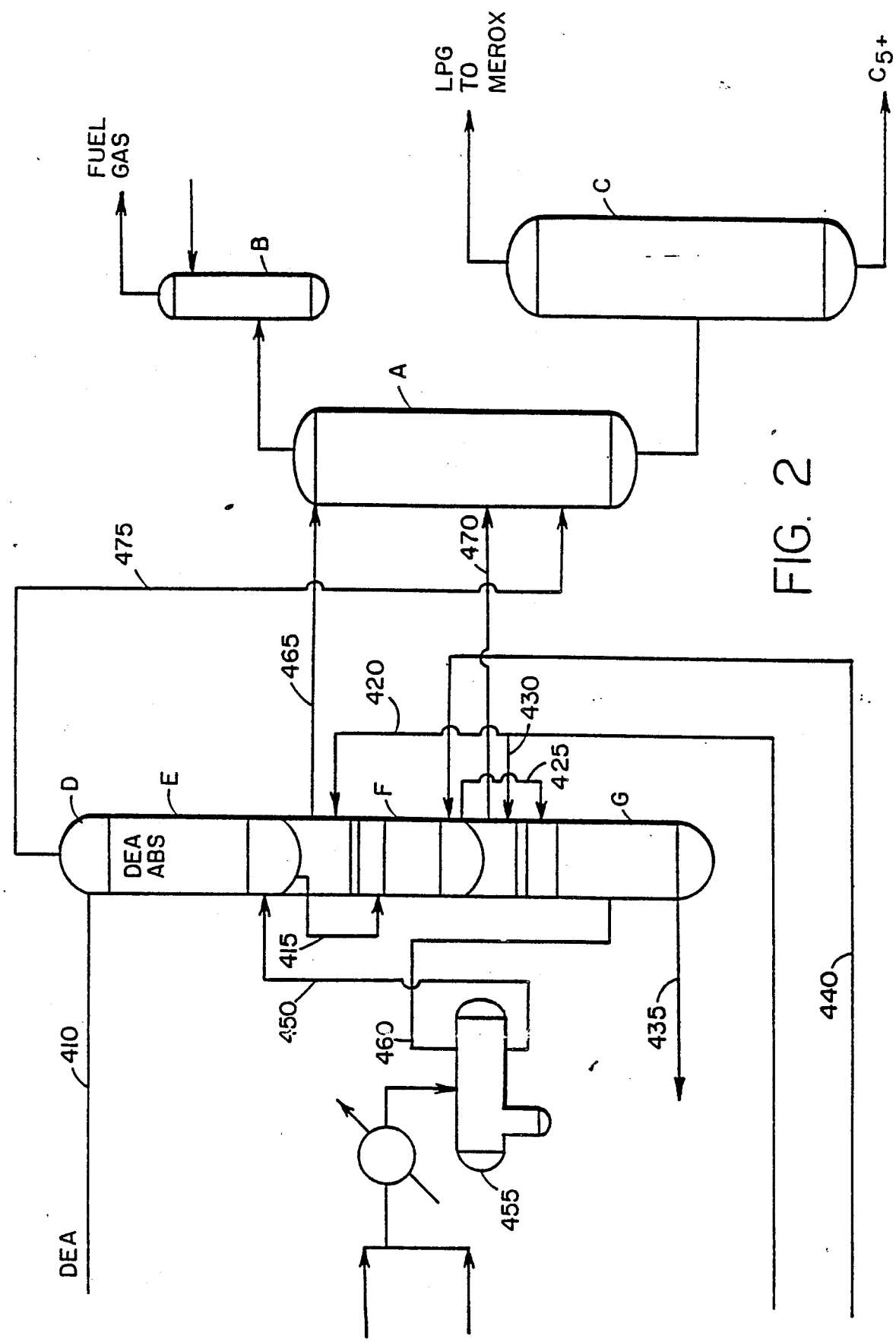
FIG. 2 is a schematic diagram showing the major processing steps of a second embodiment of the intermediate product fractionation section of the invention which may optionally be used to effect higher $C_4-$ aliphatics recovery.

Referring now to FIG. 2, a higher recovery variation of the intermediate product fractionation stage of the instant invention is presented. As in the embodiment of the intermediate product fractionation stage of this invention described above with reference to FIG. 1, the USGP separation zones A, B, and C are located downstream of the DEA amine absorber D. In the embodiment of the intermediate product fractionation stage described in FIG. 2, however, absorber D contains three separate but interconnected amine absorber zones E, F, and G, each of which are fed with a fresh amine stream. Lean DEA is introduced through line 410 into a top portion of zone D. Partially spent DEA flows through line 415 from a bottom portion of zone E to the top of zone F. Fresh DEA is added to the top of zone F via line 420. Partially spent DEA is withdrawn from the bottom of zone F is charged to the top of zone G through line 425 together with fresh DEA which is added to the top of zone G through line 430. Rich DEA is withdrawn from a bottom portion of zone G. Unstabilized gasoline flows through line 440 into the bottom portion of zone F countercurrent to the flow of DEA. The liquid fraction from separator 455 is introduced to the bottom portion of zone E via line 450, also countercurrent to the flow of DEA while the vapor portion is passed throuqh line 460 from the separator is passed to the lower portion of zone F.

Deacidified unstabilized gasoline is withdrawn from a bottom portion of zone E via line 465 and introduced to a top portion of the deethanizer--absorber zone A. The deacidified vapor fraction is transferred via line 470 to the mid portion or lower portion of zone A from a bottom portion of zone F while an overhead stream from zone E is introduced into a lower portion of deethanizer-absorber zone A.

As in the previously described configuration, the deacidified effluents from zone A are further treated and separated in sponge absorber B and debutanizer C to produce deacidified fuel gas, deacidified LPG, and deacidified $C_5$ hydrocarbons.

In the intermediate product fractionation stage described in FIG. 2, the three deethanizer-absorber feedstreams including the high pressure separator liquid, high pressure separator vapor, and FCC unstabilized gasoline are amine treated in three amine absorbers. In this design the USGP LPG recovery is improved due to higher hydrocarbons partial pressure in the deethanizer-absorber and sponge absorber and deacidification after removing the recoverable acids and $CO_2$.

The unique deacidification configuration of the intermediate product fractionation stages described above with reference to FIGS. 1 and 2 allows the deethanizer to be controlled to shift ethane/ethylene to the bottom stream rather than to take the bulk of the $C_2$ material overhead as fuel gas. This operational flexibility is enhanced by upstream deacidification, and allows the debutanizer to produce an overhead gas stream containing not only $C_3$-$C_4$ aliphatics but also a substantial portion of the $C_2$ hydrocarbons produced in the cracking process. Further, shifting the deethanizer cut point tends to reduce the relative hydrogen concentration in the debutanizer overhead stream so that the light $C_2$-$C_5$ aliphatics may be catalytically upgraded under relatively severe temperature conditions without incurring incremental capital costs for high alloy process equipment.

The Light Aliphatics Upgrading Stage

The final stage of the process of the present invention upgrades the purified intermediate $C_2$-$C_4$ product stream via aromatization, oligomerization, or etherification.

Aromatization

The following representative U.S. patents exemplify the feed compositions and process conditions for aliphatics aromatization reactions compatible with the final stage of the present process.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline U.S. Pat. No. 3,760,024, incorporated by reference as if set forth at length herein, teaches a process for the preparation of aromatic compounds involving contacting a feed consisting essentially of $C_2$–$C_4$ paraffins and/or olefins with a crystalline aluminosilicate, e.g. ZSM-5.

The article "M2 Forming-A Process for Aromatization of Light Hydrocarbons" by N. Y. Chen and T. Y. Yan, 25 IND. ENG. CHEM. PROCESS DES. DEV. 151 (1986) discusses the mechanisms of dehydrogenation and aromatization and is incorporated by reference as if set forth at length herein, but is not presented to limit the invention by theory.

Etherification

The $C_2$–$C_4$ intermediate product stream may also be upgraded to a high octane gasoline blending component by etherification. The most desirable aliphatic feedstock for etherification is rich in isobutylene which may be reacted with methanol over an acidic catalyst to produce methyl-tertiary butyl ether (MTBE). Isoamylenes may also be reacted with methanol over an acidic catalyst to produce tertiary-amyl methyl ether (TAME). Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt%. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites The etherification process of the intermediate product upgrading stage most preferably includes not only the catalytic etherification reaction but also an acid zeolite catalyzed olefin oligomerization reaction to maximize yield and to simplify product separation. The etherification and the oligomerization reaction zones are operatively connected in a synergistic combination whereby etherification reaction effluent is utilized to provide additional reactive tertiary olefins by zeolite catalysis to provide olefin interconversion and oxygenate conversion. This improved etherification process is commonly known as the Mobil Olefins to Etherates and Gasoline Process (MOEG). U.S. Pat. Nos. 4,788,365; 4,826,527; 4,830,635; 4,835,329; 4,854,939; and 4,885,421 to Harandi and Owen as well as U.S. Pat. No. 4,886,925 to Harandi teach integrated etherification/interconversion processes and are incorporated herein by reference for details of the MOEG process.

Isomerization, polymerization/ oligomerization, alkylation and cracking reactions may be controlled in the acid catalysis zone to obtain a desirable distribution of normally liquid hydrocarbons useful in making gasoline and distillate range fuels. Advantageously, at least a portion of the gasoline range hydrocarbons are recovered with $C_5+$ etherate octane enhancers useful in quality motor fuels. MTBE and TAME are preferred etherates.

The reaction of methanol with isobutylene and isoamylenes at moderate conditions with a resin catalyst is known technology, as provided by R W. Reynolds, et al., *The Oil and Gas Journal* June 16, 1975, and S. Pecci and T. Floris, *Hydrocarbon Processing*, December, 1977. An article entitled "MTBE and TAME - A Good Octane Boosting Combo," by J. D. Chase, et al., *The Oil and Gas Journal,* Apr. 9, 1979, pages 149–152, discusses the technology. A preferred catalyst is a bifunctional ion exchange resin which etherifies and isomerizes the reactant streams. A typical acid catalyst is Amberlyst 15 sulfonic acid resin, MTBE and TAME are known to be high octane ethers. The article by J. D. Chase, et al., *Oil and Gas Journal,* Apr. 9, 1979, discusses the advantages one can achieve by using these materials to enhance gasoline octane. The octane blending number of MTBE when 10% is added to a base fuel ($R+0=91$) is about 120. For a fuel with a low motor rating ($M+0=83$) octane, the blending value of MTBE at the 10% level is about 103. On the other hand, for an ($R+0$) of 95 octane fuel, the blending value of 10% MTBE is about 114.

Processes for producing and recovering MTBE and other methyl tertiary alkyl ethers from $C_4$–$C_7$ isoolefins are known to those skilled in the art, such as disclosed in U.S. Pat. Nos. 4,544,776 to Osterburq, et al. and 4,603,225 to Colaianne et al. Various suitable extraction and distillation techniques are known for recovering ether and hydrocarbon streams from etherification effluent.

Interconversion/Oligomerization

The final aliphatics upgrading stage may also comprise olefins interconversion or oligomerization. This process is commonly known as the Mobil Olefins to Gasoline/Distillate/Lubricants Process (MOG/MOGD/MOGDL). Operating details for typical MOGD units are disclosed in U.S. Pat. Nos. 4,456,779; 4,497,968 to Owen et al.; and 4,433,185 to Tabak, which are incorporated herein by reference.

In the process for catalytic conversion of olefins to heavier hydrocarbons by catalytic oligomerization using an acid crystalline zeolite, such as ZSM-5, process conditions can be varied to favor the formation of either gasoline, distillate or lube range products. At moderate temperature and relatively high pressure, the conversion conditions favor distillate range product having a normal boiling point of at least 165° C. (330° F.). Lower olefinic feedstocks containing $C_2$–$C_5$ alkenes may be converted selectively; however, the low severity distillate mode conditions cannot completely convert the fraction of ethene in the feed. Propene, butenes and others may be converted to the extent of more than 95% per pass in the distillate mode.

In the MOGD process, light olefins are oligomerized to high molecular weight distillate range olefins over ZSM-5. In that process olefin molecular weight growth through a sequence of oligomerization and cracking reactions is thermodynamically forced at relatively high pressures of about 5600 kPa (800 psia) and relatively low temperatures of about 260° C. (500° F.). At much lower pressure, thermodynamics restrict the olefin distribution to low molecular weight. This is the basis for the olefin interconversion process, i.e., to operate under conditions where lower olefins, such as $C_2$-$C_4$ olefins can be converted to an equilibrium distribution of olefins with butenes and pentenes maximized. While providing redistribution or interconversion of olefins, it has been discovered that under such interconversion conditions lower oxygenates, such as methanol, are also converted to olefins in the presence of ZSM-5 catalyst when the reaction temperature is above 204° C. (400° F.). Thus the most preferred embodiment of the etherification stage described above, MOEG, includes an olefin interconversion reaction.

The olefin interconversion process as utilized in the present invention can use fixed bed, moving bed or fluid bed reactors containing zeolite type catalysts such as ZSM-5. Operating conditions encompass temperatures between 200° and 400° C. and low pressures, generally between 100 and 500 kPa.

Process Flow Description for the Preferred Embodiment

Figure 3:
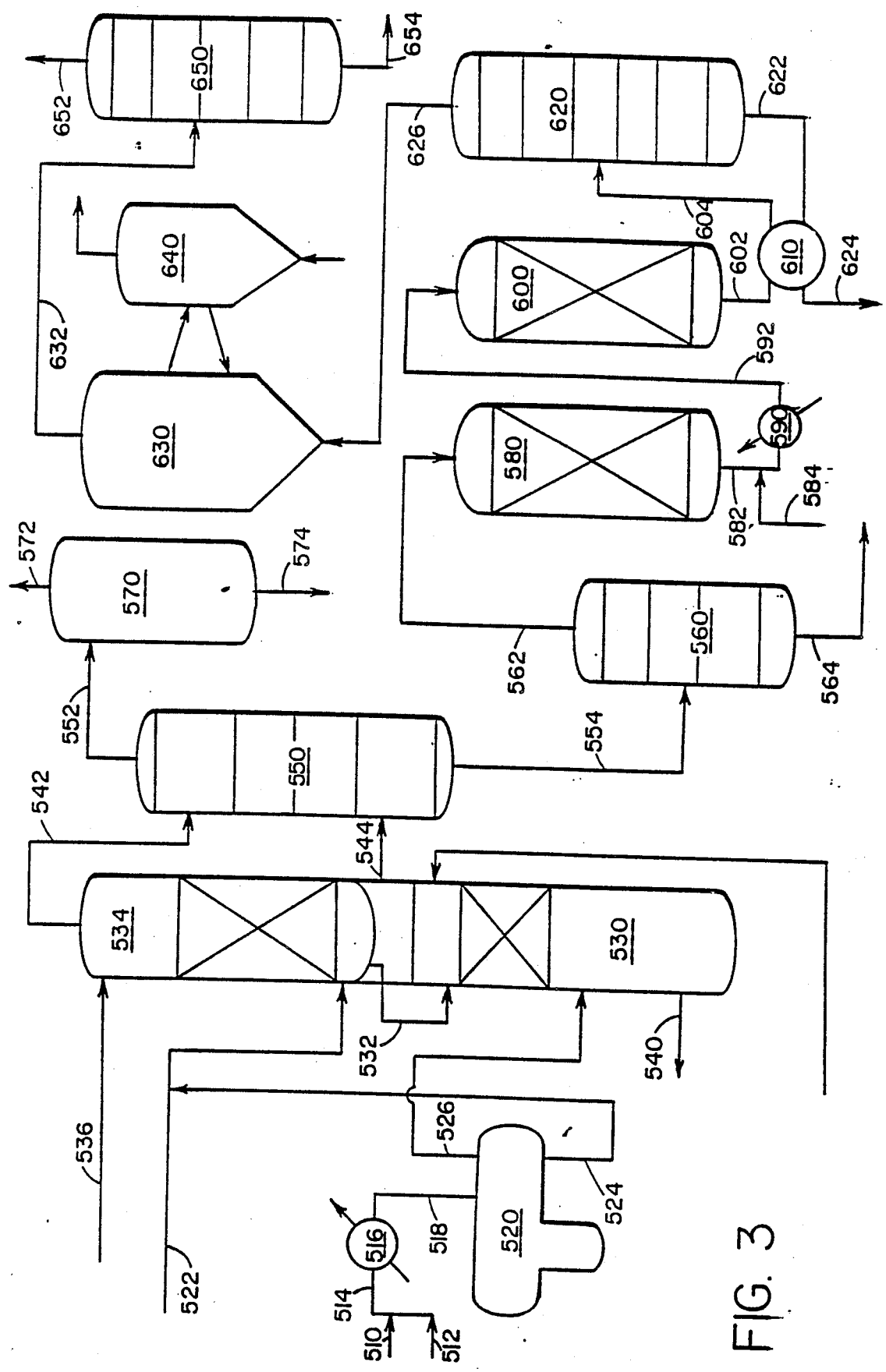
FIG. 3 is a simplified schematic diagram showing major processing steps of the intermediate product fractionation and light aliphatics upgrading stages of the present invention.

Referring now to FIG. 3, wet gas compressor interstage liquid and wet gas compressor outlet liquid flowing through lines 510 and 512, respectively, mix and flow to cooler 516 via line 514. The cooled mixture, typically rich in $C_5-$ olefins, enters accumulator drum 520 through line 518 where it is flashed to a liquid fraction which flows to unstabilized gasoline charge line 522 through line 524 and a light olefinic gas which is withdrawn from accumulator drum 520 via overhead line 526.

The accumulator bottom stream together with the unstabilized gasoline flow through line 522 to a bottom section of primary amine absorber 534 in countercurrent flow with a lean diethanolamine (DEA) mixture entering the top of primary amine absorber 534 through line 536. Partially spent DEA is withdrawn from a lower section of primary amine absorber 534 through line and enters an upper section of secondary amine absorber 530 together with fresh DEA entering the secondary amine absorber through line 538.

Light olefinic gas flowing overhead from accumulator drum 520 through line 526 enters a lower portion of secondary amine absorber 530 in countercurrent flow with DEA. The acid-enriched DEA is withdrawn from a lower portion of secondary amine absorber 530 through line 540.

Deacidified unstabilized gasoline flows overhead from primary amine absorber 534 through line 542 to an upper tray of demethanizer absorber/stripper 550. Deacidified light olefinic gas flows through line 544 from an upper section of secondary amine absorber 530 to a lower tray of demethanizer absorber/stripper 550. The overhead stream from demethanizer absorber/stripper 550 is rich in methane and may be burned as fuel gas. The demethanizer overhead stream is, however, preferably treated in sponge absorber/stripper 570 which further separates methane taken overhead through line 572 for fuel gas. The demethanizer absorber/stripper bottom stream, rich in $C_2+$ alphatics, flows to a middle tray of debutanizer 560 via line 554.

Debutanizer 560 fractionates the demethanizer absorber/stripper bottom stream into a $C_5+$ stabilized gasoline product stream, which is sent to blending or storage facilities through line 564, and an overhead stream rich in $C_4-$ aliphatics. The operation of debutanizer 560 differs from that typical of catalytic cracking unit unsaturate gas plant debutanizers in that the bottom temperature is increased to permit at least a portion of the $C_5$ components to flow overhead.

The debutanzer overhead stream may be routed directly to a zeolite-catalyzed aliphatics upgrading reaction such as aromatization, interconversion, or oligomerizaiton as described above (not shown). However, in the most preferred embodiment, the intermediate product upgrading stage of the present invention comprises an etherification/interconversion process, referred to above as MOEG.

The debutanizer overhead stream is then charged to guard chamber 580 which is preferably filled with a guard bed of bifunctional ion exchange resin similar to that contained in the downstream etherification reactor 600. A water wash may optionally be used instead of a guard chamber. The guard bed of catalyst sorbs impurities such as nitrogen compounds from the feed to prolong the life of the catalyst in the downstream reactors. The purified aliphatic stream flows out of guard chamber 580 through line 582 and is mixed with an oxygenate, preferably methanol, injected into line 582 through line 584 to form an etherification charge stream. The etherification charge stream flows to cooler 590 and then to etherification reactor 600.

A product stream rich in methyl tertiary butyl ether (MTBE) and tertiary amyl methyl ether (TAME) flows via line 602 from the bottom of etherification reactor 600 through feed/bottoms exchanger 610 and line 604 to a middle tray of etherification product fractionator 620. A high octane gasoline stream rich in MTBE and TAME is withdrawn from fractionator 620 via line 622 and passes through feed/bottoms exchanger 610 and line 624 as it is routed to gasoline blending facilities or to storage.

The overhead product stream from etherification product fractionator 620 contains both unreacted methanol and $C_4-$ olefins. This mixture is charged via line 626 to reactor 630 which contains a bed of medium-pore zeolite catalyst. Reactor 630 is preferably a fluid bed reactor coupled with a continuous catalyst regeneration unit 640.

Reactor effluent product rich in $C_5+$ gasoline is withdrawn from reactor 630 through line 632 and is charged to debutanizer fractionator 650 where it is split into a $C_4-$ overhead stream flowing overhead from debutanizer fractionator 650 through line 652 and a $C_5+$ gasoline stream flowing from the bottom of debutanizer fractionator 650 through line 654.

Changes and modifications in the specifically described embodiments can be carried out without departing from the scope of the invention which is intended to be limited only by the scope of the appended claims.

What is claimed is:

1. A process for upgrading light olefinic crackate gas from a hydrocarbon cracking comprising the sequential steps of:
    (a) compressing and cooling a $C_4-$ cracking process product stream to provide an ethene-rich vapor stream and a first condensed $C_3+$ aliphatic stream;
    (b) deacidifying said ethene-rich vapor stream and said first condensed $C_3+$ aliphatic stream by countercurrently contacting said ethene-rich vapor stream and said first condensed $C_3+$ aliphatic stream with acid absorbant;

(c) countercurrently contacting said deacidified ethene-rich vapor stream and said deacidified condensed $C_{3+}$ aliphatic stream with a $C_{5+}$ liquid sorbent stream comprising a cracking gasoline under superatmospheric pressure in an absorber column to sorb a major portion of $C_{2+}$ components;

(d) recovering a methane-rich overhead stream from said absorber column;

(e) recovering an absorber bottom stream from said absorber column containing $C_{2+}$ components; (f) fractionating said absorbes bottom stream in a first fractionator to evolve an overhead stream rich in $C_2$–$C_5$ aliphatics and a $C_{5+}$ cracking gasoline bottom stream;

(g) mixing at least a portion of said overhead stream of step (f) above with an amount of a primary alcohol sufficient to etherify the $C_4C_5$ olefins contained in said overhead stream;

(h) contacting said mixture of step (g), above, with an acid etherification catalyst under etherification conversion conditions to form a product mixture containing high-octane gasoline rich in ethers as well as unconverted oxygenate and $C_4-$ aliphatic hydrocarbons;

(i) fractionating said high octane gasoline product mixture of step (h) above, in a second fractionator into an overhead stream containing unconverted oxygenate and $C_4-$ aliphatics and a bottom stream containing ether-rich high octane gasoline; and (j) contacting said second fractionator overhead stream with a zeolite having a Constraint Index between about 1 and about 12 under aliphatic/alcohol conversion conditions to upgrade the unconverted oxygenate and aliphatics contained in said second fractionator overhead stream to $C_{5+}$ gasoline.

2. The process of claim 1 wherein said acid absorbent comprises an amine.

3. The process of claim 2 further comprising contacting said $C_{5+}$ liquid sorbent with said lean acid-sorbing absorbent in said absorption zone.

4. The process of claim 3 wherein said $C_{5+}$ liquid sorbent comprises at least a portion of said $C_{5+}$ cracking gasoline of step (e), above.

5. The process of claim 2 wherein said absorbent is ethanolamine.

6. The process of claim 5 wherein said ethanolamine comprises at least one selected from the group consisting of monoethanolamine, deithanolamine and triethanolamine.

7. The process of claim 1 wherein said acid etherification catalyst comprises a sulfonic acid resin.

8. The process of claim 1 further comprising mixing effluent from said guard bed of step (f) above with sufficient primary alcohol to provide an alcohol: $C_4$–$C_5$ tertiary olefin mole ratio of between about 0.7 and about 1.1.

9. The process of claim 1 wherein said zeolite of step (j) has the structure of at least one selected from the group consisting of ZSM-5, ZSM-11, ZSM-12, ZSM-23, ZSM-35 and ZSM-48.

10. The process of claim 1 wherein said etherification conversion conditions include temperatures of about 30° C. to about 150° C., pressures of about 700 kPa to about 3500 kPa and weight hourly space velocities of about 1 $hr^{-1}$ to about 20 $hr^{-1}$.

11. The process of claim 1 wherein said aliphatic/alcohol conversion conditions of step (j), above include temperatures of about 300° C. to about 700° C., pressures of about 300 kPa to about 700 kPa and weight hourly space velocities of about 0.4 $hr^{-1}$ to about 20 $hr^{-1}$.

12. A process for upgrading light olefinic crackate gas from hydrocarbon cracking comprising the sequential steps of:

(a) compressing and cooling a $C_4-$ catalytic cracking process product stream to provide an ethene-rich vapor stream and a first condensed $C_{3+}$ aliphatic stream;

(b) deacidifying said ethene-rich vapor stream and said first condensed $C_{3+}$ aliphatic stream by countercurrently contacting said ethene-rich vapor stream and said first condensed $C_{3+}$ aliphatic stream with acid absorbant;

(c) countercurrently contacting said deacidified ethene-rich vapor stream and said deacidified condensed $C_{3+}$ aliphatic stream with a $C_{5+}$ liquid sorbent stream comprising a catalytic cracking gasoline under superatmospheric pressure in an absorber/stripper column to sorb a major portion of $C_{2+}$ components;

(d) recovering a methane-rich overhead stream from said absorber/stripper column;

(e) recovering an absorber/stripper bottom stream from said absorber/stripper column containing $C_{2+}$ components;

(f) fractionating said absorber/stripper bottom stream in a first fractionator to evolve an overhead stream rich in $C_2$–$C_5$ aliphatics and a $C_{5+}$ catalytic cracking gasoline bottom stream;

(g) contacting said first fractionator overhead stream with an acid etherification catalyst in a guard bed zone to sorb at least a portion of the catalyst poisons in said debutanizer overhead stream including sulfur- and nitrogen-containing compounds;

(h) mixing effluent from said guard bed of step (f) above with an amount of a primary alcohol sufficient to etherify the $C_4$–$C_5$ olefins contained in said guard bed effluent;

(i) contacting said mixture of primary alcohol and guard bed effluent of step (h), above, with an acid etherification catalyst under etherification conversion conditions to form a product mixture containing high-octane gasoline rich in ethers as well as unconverted oxygenate and $C_4-$ aliphatic hydrocarbons;

(j) fractionating said high octane gasoline product mixture of step (i) above, in a second fractionator into an overhead stream containing unconverted oxygenate and $C_4-$ aliphatics and a bottom stream containing ether-rich high octane gasoline; and (k) contacting said second fractionator overhead stream with a zeolite having a Constraint Index between about 1 and about 12 under aliphatic/alcohol conversion conditions to upgrade the unconverted oxygenate and aliphatics contained in said second fractionator overhead stream to $C_{5+}$ gasoline.

* * * * *

UNITED STATES PATENT AND TRADEMARK OFFICE
CERTIFICATE OF CORRECTION

PATENT NO. : 4,990,712
DATED : February 5, 1991
INVENTOR(S) : Mohsen N. Harandi et al.

It is certified that error appears in the above-identified patent and that said Letters Patent is hereby corrected as shown below:

Col. 15, Claim 1, Lines 11-12, delete "(f)" after "components" and
   insert --(f)-- directly in front of "fractionating";
   also, "absorbes" (line 12) should read --absorber--.

Col. 15, Claim 1, line 18, "$C_4C_5$" should read --$C_4-C_5$--.

Signed and Sealed this

Eighth Day of February, 1994

*Attest:*

BRUCE LEHMAN

*Attesting Officer*     *Commissioner of Patents and Trademarks*